United States Patent
Hammerland, III (10) Patent No.: US 11,033,289 B2
(45) Date of Patent: Jun. 15, 2021

(54) JAW GUARD FOR SURGICAL FORCEPS

(71) Applicant: COVIDIEN LP, Mansfield, MA (US)

(72) Inventor: John A. Hammerland, III, Arvada, CO (US)

(73) Assignee: COVIDIEN LP, Mansfield, MA (US)

( * ) Notice: Subject to any disclaimer, the term of this patent is extended or adjusted under 35 U.S.C. 154(b) by 122 days.

(21) Appl. No.: 16/383,807

(22) Filed: Apr. 15, 2019

(65) Prior Publication Data

US 2019/0336156 A1 Nov. 7, 2019

Related U.S. Application Data

(60) Provisional application No. 62/665,640, filed on May 2, 2018.

(51) Int. Cl.
*A61B 17/295* (2006.01)
*A61B 17/28* (2006.01)
(Continued)

(52) U.S. Cl.
CPC ........ *A61B 17/295* (2013.01); *A61B 17/2804* (2013.01); *A61B 17/29* (2013.01);
(Continued)

(58) Field of Classification Search
CPC ... A61B 17/295; A61B 17/2804; A61B 17/02; A61B 18/1445; A61B 2017/293;
(Continued)

(56) References Cited

U.S. PATENT DOCUMENTS

| D249,549 S | 9/1978 | Pike |
|---|---|---|
| D263,020 S | 2/1982 | Rau, III |
| (Continued) | | |

FOREIGN PATENT DOCUMENTS

| CN | 201299462 Y | 9/2009 |
|---|---|---|
| DE | 2415263 A1 | 10/1975 |
| (Continued) | | |

OTHER PUBLICATIONS

Heniford et al. "Initial Research and Clinical Results with an Electrothermal Bipolar Vessel Sealer" Oct. 1999.
(Continued)

*Primary Examiner* — Richard G Louis
(74) *Attorney, Agent, or Firm* — Carter, DeLuca & Farrell LLP (57) ABSTRACT

An end effector assembly for a forceps includes first and second jaw members, each including a proximal flange extending therefrom. Each proximal flange defines an aperture extending therethrough configured to receive a pivot assembly including first and second pivot pins. The second proximal flange includes a U-shaped cross section having first and second legs defining a slot therebetween. A guard is disposed between the proximal flanges of the first and second jaw members and includes a U-shaped cross section with first and second legs configured to receive the proximal flange of the first jaw member and seat within the slot of the second jaw member. The guard is configured to eliminate gaps between the proximal flanges of the first and second jaw members during angular rotation of the first and second jaw members between a first, spaced apart position to a second, closer position.

19 Claims, 5 Drawing Sheets

(51) Int. Cl.
*A61B 17/29* (2006.01)
*A61B 18/14* (2006.01)
*A61B 18/00* (2006.01)

(52) U.S. Cl.
CPC .... *A61B 18/1445* (2013.01); *A61B 2017/293* (2013.01); *A61B 2017/2947* (2013.01); *A61B 2018/0063* (2013.01); *A61B 2018/1452* (2013.01)

(58) Field of Classification Search
CPC .... A61B 2018/0063; A61B 2018/1452; A61B 2017/2947; A61B 2018/1455; A61B 18/1442; A61B 2090/08021; A61B 17/2816
See application file for complete search history.

(56) References Cited

U.S. PATENT DOCUMENTS

| | | |
|---|---|---|
| D295,893 S | 5/1988 | Sharkany et al. |
| D295,894 S | 5/1988 | Sharkany et al. |
| D298,353 S | 11/1988 | Manno |
| D299,413 S | 1/1989 | DeCarolis |
| D343,453 S | 1/1994 | Noda |
| D348,930 S | 7/1994 | Olson |
| D349,341 S | 8/1994 | Lichtman et al. |
| D354,564 S | 1/1995 | Medema |
| D358,887 S | 5/1995 | Feinberg |
| D384,413 S | 9/1997 | Zlock et al. |
| H1745 H | 8/1998 | Paraschac |
| D402,028 S | 12/1998 | Grimm et al. |
| D408,018 S | 4/1999 | McNaughton |
| D416,089 S | 11/1999 | Barton et al. |
| D424,694 S | 5/2000 | Tetzlaff et al. |
| D425,201 S | 5/2000 | Tetzlaff et al. |
| H1904 H | 10/2000 | Yates et al. |
| D449,886 S | 10/2001 | Tetzlaff et al. |
| D453,923 S | 2/2002 | Olson |
| D454,951 S | 3/2002 | Bon |
| D457,958 S | 5/2002 | Dycus et al. |
| D457,959 S | 5/2002 | Tetzlaff et al. |
| H2037 H | 7/2002 | Yates et al. |
| D465,281 S | 11/2002 | Lang |
| D466,209 S | 11/2002 | Bon |
| D493,888 S | 8/2004 | Reschke |
| D496,997 S | 10/2004 | Dycus et al. |
| D499,181 S | 11/2004 | Dycus et al. |
| D502,994 S | 3/2005 | Blake, III |
| D509,297 S | 9/2005 | Wells |
| D525,361 S | 7/2006 | Hushka |
| D531,311 S | 10/2006 | Guerra et al. |
| D533,274 S | 12/2006 | Visconti et al. |
| D533,942 S | 12/2006 | Kerr et al. |
| D535,027 S | 1/2007 | James et al. |
| D538,932 S | 3/2007 | Malik |
| D541,418 S | 4/2007 | Schechter et al. |
| D541,611 S | 5/2007 | Aglassinger |
| D541,938 S | 5/2007 | Kerr et al. |
| D545,432 S | 6/2007 | Watanabe |
| D547,154 S | 7/2007 | Lee |
| D564,662 S | 3/2008 | Moses et al. |
| D567,943 S | 4/2008 | Moses et al. |
| D575,395 S | 8/2008 | Hushka |
| D575,401 S | 8/2008 | Hixson et al. |
| D582,038 S | 12/2008 | Swoyer et al. |
| D617,900 S | 6/2010 | Kingsley et al. |
| D617,901 S | 6/2010 | Unger et al. |
| D617,902 S | 6/2010 | Twomey et al. |
| D617,903 S | 6/2010 | Unger et al. |
| D618,798 S | 6/2010 | Olson et al. |
| D621,503 S | 8/2010 | Otten et al. |
| D627,462 S | 11/2010 | Kingsley |
| D628,289 S | 11/2010 | Romero |
| D628,290 S | 11/2010 | Romero |
| D630,324 S | 1/2011 | Reschke |
| D649,249 S | 11/2011 | Guerra |
| D649,643 S | 11/2011 | Allen, IV et al. |
| D661,394 S | 6/2012 | Romero et al. |
| D670,808 S | 11/2012 | Moua et al. |
| D680,220 S | 4/2013 | Rachlin |
| 9,084,608 B2 | 7/2015 | Larson et al. |
| 9,211,657 B2 | 12/2015 | Ackley et al. |
| 2014/0221995 A1 | 8/2014 | Guerra et al. |
| 2014/0221999 A1 | 8/2014 | Cunningham et al. |
| 2014/0228842 A1 | 8/2014 | Dycus et al. |
| 2014/0230243 A1 | 8/2014 | Roy et al. |
| 2014/0236149 A1 | 8/2014 | Kharin et al. |
| 2014/0243811 A1 | 8/2014 | Reschke et al. |
| 2014/0243824 A1 | 8/2014 | Gilbert |
| 2014/0249528 A1 | 9/2014 | Hixson et al. |
| 2014/0250686 A1 | 9/2014 | Hempstead et al. |
| 2014/0257274 A1 | 9/2014 | McCullough, Jr. et al. |
| 2014/0257283 A1 | 9/2014 | Johnson et al. |
| 2014/0257284 A1 | 9/2014 | Artale |
| 2014/0257285 A1 | 9/2014 | Moua |
| 2014/0276803 A1 | 9/2014 | Hart |
| 2014/0284313 A1 | 9/2014 | Allen, IV et al. |
| 2014/0288549 A1 | 9/2014 | McKenna et al. |
| 2014/0288553 A1 | 9/2014 | Johnson et al. |
| 2014/0330308 A1 | 11/2014 | Hart et al. |
| 2014/0336635 A1 | 11/2014 | Hart et al. |
| 2014/0353188 A1 | 12/2014 | Reschke et al. |
| 2015/0018816 A1 | 1/2015 | Latimer |
| 2015/0025528 A1 | 1/2015 | Arts |
| 2015/0032106 A1 | 1/2015 | Rachlin |
| 2015/0051598 A1 | 2/2015 | Orszulak et al. |
| 2015/0051640 A1 | 2/2015 | Twomey et al. |
| 2015/0066026 A1 | 3/2015 | Hart et al. |
| 2015/0080880 A1 | 3/2015 | Sartor et al. |
| 2015/0080889 A1 | 3/2015 | Cunningham et al. |
| 2015/0082928 A1 | 3/2015 | Kappus et al. |
| 2015/0088122 A1 | 3/2015 | Jensen |
| 2015/0088126 A1 | 3/2015 | Duffin et al. |
| 2015/0088128 A1 | 3/2015 | Couture |
| 2015/0094714 A1 | 4/2015 | Lee et al. |

FOREIGN PATENT DOCUMENTS

| | | |
|---|---|---|
| DE | 02514501 A1 | 10/1976 |
| DE | 2627679 A1 | 1/1977 |
| DE | 03423356 C2 | 6/1986 |
| DE | 03612646 A1 | 4/1987 |
| DE | 3627221 A1 | 2/1988 |
| DE | 8712328 U1 | 3/1988 |
| DE | 04303882 C2 | 2/1995 |
| DE | 04403252 A1 | 8/1995 |
| DE | 19515914 C1 | 7/1996 |
| DE | 19506363 A1 | 8/1996 |
| DE | 29616210 U1 | 11/1996 |
| DE | 19608716 C1 | 4/1997 |
| DE | 19751106 A1 | 5/1998 |
| DE | 19751108 A1 | 5/1999 |
| DE | 19946527 C1 | 7/2001 |
| DE | 20121161 U1 | 4/2002 |
| DE | 10045375 C2 | 10/2002 |
| DE | 202007009165 U1 | 8/2007 |
| DE | 202007009317 U1 | 8/2007 |
| DE | 202007009318 U1 | 8/2007 |
| DE | 10031773 B4 | 11/2007 |
| DE | 202007016233 U1 | 1/2008 |
| DE | 19738457 B4 | 1/2009 |
| DE | 102004026179 B4 | 1/2009 |
| DE | 102008018406 B3 | 7/2009 |
| EP | 1281878 A1 | 2/2003 |
| EP | 1159926 A2 | 3/2003 |
| JP | 61501068 | 9/1984 |
| JP | 1024051 A | 1/1989 |
| JP | 1147150 A | 6/1989 |
| JP | 6502328 | 3/1992 |
| JP | 55106 | 1/1993 |
| JP | H0540112 A | 2/1993 |
| JP | 6121797 A | 5/1994 |
| JP | 6285078 A | 10/1994 |

(56) References Cited

FOREIGN PATENT DOCUMENTS

| | | |
|---|---|---|
| JP | 6511401 | 12/1994 |
| JP | H06343644 A | 12/1994 |
| JP | H07265328 A | 10/1995 |
| JP | 08056955 | 3/1996 |
| JP | 08252263 A | 10/1996 |
| JP | 8289895 A | 11/1996 |
| JP | 8317934 A | 12/1996 |
| JP | 8317936 A | 12/1996 |
| JP | 09000538 A | 1/1997 |
| JP | H0910223 A | 1/1997 |
| JP | 9122138 A | 5/1997 |
| JP | 0010000195 A | 1/1998 |
| JP | 10155798 A | 6/1998 |
| JP | 1147149 | 2/1999 |
| JP | 11070124 A | 3/1999 |
| JP | 11169381 A | 6/1999 |
| JP | 11192238 A | 7/1999 |
| JP | H11244298 A | 9/1999 |
| JP | 2000102545 A | 4/2000 |
| JP | 2000135222 A | 5/2000 |
| JP | 2000342599 A | 12/2000 |
| JP | 2000350732 A | 12/2000 |
| JP | 2001008944 | 1/2001 |
| JP | 2001029355 | 2/2001 |
| JP | 2001029356 | 2/2001 |
| JP | 2001003400 | 4/2001 |
| JP | 2001128990 A | 5/2001 |
| JP | 2001190564 A | 7/2001 |
| JP | 2002136525 A | 5/2002 |
| JP | 2002528166 A | 9/2002 |
| JP | 2003116871 A | 4/2003 |
| JP | 2003175052 A | 6/2003 |
| JP | 2003245285 A | 9/2003 |
| JP | 2004517668 A | 6/2004 |
| JP | 2004528869 A | 9/2004 |
| JP | 2005152663 A | 6/2005 |
| JP | 2005253789 A | 9/2005 |
| JP | 2005312807 A | 11/2005 |
| JP | 2006015078 A | 1/2006 |
| JP | 2006501939 A | 1/2006 |
| JP | 2006095316 A | 4/2006 |
| JP | 2008054926 A | 3/2008 |
| JP | 2011125195 A | 6/2011 |
| JP | H0630945 B2 | 11/2016 |
| SU | 401367 A1 | 11/1974 |
| WO | 0036986 A1 | 6/2000 |
| WO | 0059392 A1 | 10/2000 |
| WO | 0115614 A1 | 3/2001 |
| WO | 0154604 A1 | 8/2001 |
| WO | 0245589 | 6/2002 |
| WO | 2006021269 A1 | 3/2006 |
| WO | 2005110264 A2 | 4/2006 |
| WO | 2008040483 A1 | 4/2008 |
| WO | 2011018154 A1 | 2/2011 |

OTHER PUBLICATIONS

Michael Choti, "Abdominoperineal Resection with the LigaSure Vessel Sealing System and LigaSure Atlas 20 cm Open Instrument" ; Innovations That Work, Jun. 2003.

Chung et al., "Clinical Experience of Sutureless Closed Hemorrhoidectomy with LigaSure" Diseases of the Colon & Rectum vol. 46, No. 1 Jan. 2003.

Tinkcler L.F., "Combined Diathermy and Suction Forceps", Feb. 6, 1967 (Feb. 6, 1967), British Medical Journal Feb. 6, 1976, vol. 1, nr. 5431 p. 361, ISSN: 0007-1447.

Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center,Charlotte,NC; Date: Aug. 2003.

Peterson et al. "Comparison of Healing Process Following Ligation with Sutures and Bipolar Vessel Sealing" Surgical Technology International (2001).

"Electrosurgery: A Historical Overview" Innovations in Electrosurgery; Sales/Product Literature; Dec. 31, 2000. (6 pages).

Johnson et al. "Evaluation of a Bipolar Electrothermal Vessel Sealing Device in Hemorrhoidectomy" Sales/Product Literature; Jan. 2004. (1 page).

E. David Crawford "Evaluation of a New Vessel Sealing Device in Urologic Cancer Surgery" Sales/Product Literature 2000.

Johnson et al. "Evaluation of the LigaSure Vessel Sealing System in Hemorrhoidectormy" American College of Surgeons (ACS) Clinicla Congress Poster (2000).

Muller et al., "Extended Left Hemicolectomy Using the LigaSure Vessel Sealing System" Innovations That Work, Sep. 1999.

Kennedy et al. "High-burst-strength, feedback-controlled bipolar vessel sealing" Surgical Endoscopy (1998) 12: 876-878.

Burdette et al. "In Vivo Probe Measurement Technique for Determining Dielectric Properties At VHF Through Microwave Frequencies", IEEE Transactions on Microwave Theory and Techniques, vol. MTT-28, No. 4, Apr. 1980 pp. 414-427.

Carus et al., "Initial Experience With the LigaSure Vessel Sealing System in Abdominal Surgery" Innovations That Work, Jun. 2002.

Heniford et al. "Initial Results with an Electrothermal Bipolar Vessel Sealer" Surgical Endoscopy (2000) 15:799-801. (4 pages).

Herman et al., "Laparoscopic Intestinal Resection With the LigaSure Vessel Sealing System: A Case Report"; Innovations That Work, Feb. 2002.

Koyle et al., "Laparoscopic Palomo Varicocele Ligation in Children and Adolescents" Pediatric Endosurgery & Innovative Techniques, vol. 6, No. 1, 2002.

W. Scott Helton, "LigaSure Vessel Sealing System: Revolutionary Hemostasis Product for General Surgery"; Sales/Product Literature 1999.

LigaSure Vessel Sealing System, the Seal of Confidence in General, Gynecologic, Urologic, and Laparaoscopic Surgery; Sales/Product Literature; Apr. 2002.

Joseph Ortenberg "LigaSure System Used in Laparoscopic 1st and 2nd Stage Orchiopexy" Innovations That Work, Nov. 2002.

Sigel et al. "The Mechanism of Blood Vessel Closure by High Frequency Electrocoagulation" Surgery Gynecology & Obstetrics, Oct. 1965 pp. 823-831.

Sampayan et al, "Multilayer Ultra-High Gradient Insulator Technology" Discharges and Electrical Insulation in Vacuum, 1998. Netherlands Aug. 17-21, 1998; vol. 2, pp. 740-743.

Paul G. Horgan, "A Novel Technique for Parenchymal Division During Hepatectomy" The American Journal of Surgery, vol. 181, No. 3, Apr. 2001 pp. 236-237.

Benaron et al., "Optical Time-Of-Flight and Absorbance Imaging of Biologic Media", Science, American Association for the Advancement of Science, Washington, DC, vol. 259, Mar. 5, 1993, pp. 1463-1466.

Olsson et al. "Radical Cystectomy in Females" Current Surgical Techniques in Urology, vol. 14, Issue 3, 2001.

Palazzo et al. "Randomized clinical trial of Ligasure versus open haemorrhoidectomy" British Journal of Surgery 2002, 89, 154-157.

Levy et al. "Randomized Trial of Suture Versus Electrosurgical Bipolar Vessel Sealing in Vaginal Hysterectomy" Obstetrics & Gynecology, vol. 102, No. 1, Jul. 2003.

"Reducing Needlestick Injuries in the Operating Room" Sales/Product Literature 2001. (1 page).

Bergdahl et al. "Studies on Coagulation and the Development of an Automatic Computerized Bipolar Coagulator" J. Neurosurg, vol. 75, Jul. 1991, pp. 148-151.

Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.

Sayfan et al. "Sutureless Closed Hemorrhoidectomy: A New Technique" Annals of Surgery vol. 234 No. 1 Jul. 2001; pp. 21-24.

Levy et al., "Update on Hysterectomy—New Technologies and Techniques" OBG Management, Feb. 2003. (15 pages).

Dulemba et al. "Use of a Bipolar Electrothermal Vessel Sealer in Laparoscopically Assisted Vaginal Hysterectomy" Sales/Product Literature; Jan. 2004.

(56) References Cited

OTHER PUBLICATIONS

Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.

Sengupta et al., "Use of a Computer-Controlled Bipolar Diathermy System in Radical Prostatectomies and Other Open Urological Surgery" ANZ Journal of Surgery (2001) 71.9 pp. 538-540.

Rothenberg et al. "Use of the LigaSure Vessel Sealing System in Minimally Invasive Surgery in Children" Int'l Pediatric Endosurgery Group (IPEG) 2000.

Crawford et al. "Use of the LigaSure Vessel Sealing System in Urologic Cancer Surger" Grand Rounds in Urology 1999 vol. 1 Issue 4 pp. 10-17.

Craig Johnson, "Use of the LigaSure Vessel Sealing System in Bloodless Hemorrhoidectomy" Innovations That Work, Mar. 2000.

Levy et al. "Use of a New Energy-based Vessel Ligation Device During Vaginal Hysterectomy" Int'l Federation of Gynecology and Obstetrics (FIGO) World Congress 1999.

Barbara Levy, "Use of a New Vessel Ligation Device During Vaginal Hysterectomy" FIGO 2000, Washington, D.C.. (1 page).

E. David Crawford "Use of a Novel Vessel Sealing Technology in Management of the Dorsal Veinous Complex" Sales/Product Literature 2000.

Jarrett et al., "Use of the LigaSure Vessel Sealing System for Peri-Hilar Vessels in Laparoscopic Nephrectomy" Sales/Product Literature 2000.

Crouch et al. "A Velocity-Dependent Model for Needle Insertion in Soft Tissue" MICCAI 2005; LNCS 3750 pp. 624-632, Dated: 2005.

McLellan et al. "Vessel Sealing for Hemostasis During Pelvic Surgery" Int'l Federation of Gynecology and Obstetrics FIGO World Congress 2000, Washington, D.C.

McLellan et al. "Vessel Sealing for Hemostasis During Gynecologic Surgery" Sales/Product Literature 1999.

U.S. Appl. No. 08/926,869, filed Sep. 10, 1997; inventor: James G. Chandler, Abandoned.

U.S. Appl. No. 09/177,950, filed Oct. 23, 1998; inventor: Randel A. Frazier, abandoned.

U.S. Appl. No. 09/387,883, filed Sep. 1, 1999; inventor: Dale F. Schmaltz, abandoned.

U.S. Appl. No. 09/591,328, filed Jun. 9, 2000; inventor: Thomas P. Ryan, abandoned.

U.S. Appl. No. 12/336,970, filed Dec. 17, 2008; inventor: Paul R. Sremcich, abandoned.

U.S. Appl. No. 14/065,644, filed Oct. 29, 2013; inventor: Reschke, abandoned.

JAW GUARD FOR SURGICAL FORCEPS

CROSS REFERENCE TO RELATED APPLICATION

The present application claims the benefit of and priority to U.S. Provisional Application Ser. No. 62/665,640, filed on May 2, 2018 the entire contents of which are incorporated herein by reference.

BACKGROUND

Technical Field

The present disclosure relates to surgical instruments and, more particularly, to an open surgical forceps for grasping, sealing, and/or dividing tissue.

Description of Related Art

A forceps is a plier-like instrument which relies on mechanical action between its jaws to grasp, clamp and constrict vessels or tissue. Electrosurgical forceps utilize both mechanical clamping action and electrical energy to affect hemostasis by heating tissue and blood vessels to coagulate and/or cauterize tissue. Certain surgical procedures require more than simply cauterizing tissue and rely on the unique combination of clamping pressure, precise electrosurgical energy control and gap distance (i.e., distance between opposing jaw members when closed about tissue) to "seal" tissue, vessels and certain vascular bundles.

Prior to cauterization or sealing, blunt dissection is a common technique during many surgical procedures which involves poking and spreading tissue to create an opening without the use of a blade or electrosurgical energy. For example, in liver surgery, it is common for surgeons to dissect through the liver by closing forceps' jaws on the soft parenchyma to expose the more elastic blood vessels and bile ducts. In many of these cases, the blunt dissection involves opening the jaw members very wide to spread the tissue. Unfortunately, jaw members on most vessel sealing devices or commonly sold electrosurgical forceps only open a certain distance before a gap at the back or proximal-most portion of the jaw member is exposed. These gaps may create various "pinch points" that can catch on tissue causing unwanted tissue damage during manipulation. Limiting the distance the jaw members can open to prevent these pinch points offsets the usefulness of the instrument for blunt dissection or clamping purposes.

SUMMARY

Typically, the jaw aperture on any vessel sealer or forceps is dependent on the location of the pivot point, the height or diameter of the instrument and the length of the jaw member. These variables are commonly balanced to fit the particular device's application. Adding a small guard or series of guard components on the jaw member or proximate the jaw pivot enables the jaw members to open wider and have wider jaw apertures without producing pinch points.

These guard(s) may take the form of small metal or plastic pieces similar in size and shape to jaw flags but they could take a variety of forms. The guard may connect with the adjacent jaw members so that the jaw guard assembly moves in a specific way relative to the jaw members. If the jaw members interface with the guard, the guard may be used to actuate the jaws. The guard may or may not move, relative to the jaw members, as the jaw members are opened and closed. The angular motion of the guard(s) may be dictated by the manner in which it is associated with the forceps' pivot point. There may be a plurality of guards to provide an even wider aperture or to appropriate the guard function into certain device geometries.

As used herein, the term "distal" refers to the portion that is being described which is further from a user, while the term "proximal" refers to the portion that is being described which is closer to a user.

In accordance with one aspect of the present disclosure, an end effector assembly for a forceps includes first and second jaw members each having a proximal flange extending therefrom. Each proximal flange includes an aperture defined therein that extends therethrough configured to receive a pivot assembly including first and second pivot pins. The second proximal flange includes a U-shaped cross section having first and second legs defining a slot therebetween. A guard is disposed between the proximal flanges of the first and second jaw members. The guard includes a U-shaped cross section with first and second legs configured to receive the proximal flange of the first jaw member and seat within the slot of the second jaw member. The guard is configured to eliminate gaps between the proximal flanges of the first and second jaw members during angular rotation of the first and second jaw members between a first, spaced apart position to a second, closer position.

In aspects of the present disclosure, the guard includes an aperture defined therein configured to receive the first and second pivot pins. The guard is rotatable about the first and second pivot pins during movement of the jaw members between the first and second positions. The aperture of the guard may be hourglass-shaped defining a stop that is configured to limit angular rotation of the guard when the jaw members are moved from the second position to the first position.

In other aspects of the present disclosure, an aperture in the proximal flange of the second jaw member is hourglass-shaped and defines a stop that is configured to limit angular rotation of the second jaw member when the jaw members are moved from the second position to the first position. The hourglass-shaped aperture in the proximal flange may be larger than the hourglass-shaped aperture in the guard such that the degree of angular rotation of the second jaw member is greater than the degree of angular rotation of the guard.

In yet other aspects, the pivot assembly is mechanically engaged to the proximal flange of the first jaw member by snap-fit, overmolding, injection molding and/or friction fit. In still other aspects, the pivot assembly may be integrally associated with the proximal flange of the first jaw member.

In aspects of the present disclosure, the first and second pivot pins may be configured to extend on either side of the pivot assembly to pivotably engage both legs of the U-shaped guard and both legs of the U-shaped proximal flange of the second jaw member. One or both of the first and second pivot pins may be configured to abut the stop on the aperture of the guard to limit angular rotation of the guard. One or both of the first and second pivot pins may be configured to abut the stop on the aperture of the proximal flange to limit angular rotation of the first and second jaw members from the second to first positions.

In accordance with another aspect of the present disclosure, a forceps includes first and second shaft members, the first shaft member including a first jaw member at a distal end thereof and the second shaft member including a second jaw member at a distal end thereof. The first and second jaw members are disposed in opposing relation relative to one another and are movable about a pivot assembly from a first, spaced apart position to a second, closer position for grasping tissue. Each of the jaw members includes a proximal flange extending therefrom that defines an aperture extending therethrough configured to receive the pivot assembly. The second proximal flange includes a U-shaped cross section having first and second legs that define a slot therebetween. A guard is disposed between the proximal flanges of the first and second jaw members and includes a U-shaped cross section with first and second legs configured to receive the proximal flange of the first jaw member and seat within the slot of the second jaw member. The guard is configured to eliminate gaps between the proximal flanges of the first and second jaw members during angular rotation of the first and second jaw members between the first and second positions.

BRIEF DESCRIPTION OF THE DRAWINGS

Various aspects of the present disclosure are described herein with reference to the drawings wherein like reference numerals identify similar or identical elements.

DETAILED DESCRIPTION

Figure 1:
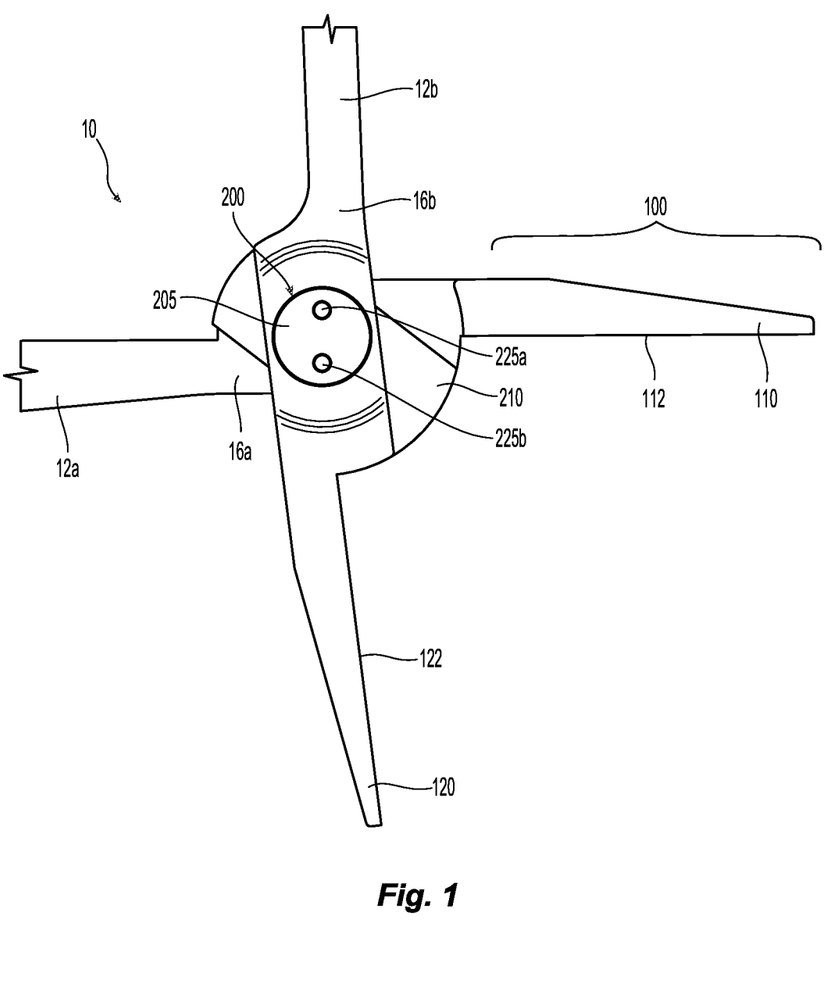
FIG. 1 is a side view of a distal end of a forceps according to an aspect of the present disclosure showing the forceps in an open configuration.

Referring now to FIG. 1, an open forceps 10 contemplated for use in connection with traditional open surgical procedures is shown. For the purposes herein, either an open instrument, e.g., forceps 10, or an endoscopic instrument (not shown) may be utilized in accordance with the present disclosure. Obviously, different electrical and mechanical connections and considerations apply to each particular type of instrument; however, the aspects of the present disclosure with respect to the end effector assembly and its operating characteristics remain generally consistent with respect to both the open and endoscopic configurations.

With continued reference to FIG. 1, forceps 10 includes two elongated shafts 12a and 12b, each having a proximal end (not shown), and a distal end 16a and 16b, respectively. Forceps 10 further includes an end effector assembly 100 attached to distal ends 16a and 16b of shafts 12a and 12b, respectively. End effector assembly 100 includes a pair of opposing jaw members 110 and 120 that are pivotably connected about a pivot assembly 200. Each shaft 12a and 12b includes a handle (not shown) disposed at the proximal end thereof. Each handle defines a finger hole therethrough for receiving a finger of the user to facilitate actuation of the forceps 10 and movement of the shaft members 12a and 12b relative to one another between a spaced-apart position and an approximated position, which, in turn, pivots jaw members 110 and 120 from an open or first position, wherein the jaw members 110 and 120 are disposed in spaced-apart relation relative to one another, to a second or closer position, wherein the jaw members 110 and 120 cooperate to grasp tissue therebetween.

A ratchet (not shown) may be included for selectively locking the jaw members 110 and 120 relative to one another at various positions during pivoting. The ratchet may include graduations or other visual markings that enable the user to easily and quickly ascertain and control the amount of closure force desired between the jaw members 110 and 120.

Continuing with reference to FIG. 1, one of the shafts, e.g., shaft 12b, may include a proximal shaft connector (not shown) that is designed to connect the forceps 10 to a source of electrosurgical energy such as an electrosurgical generator (not shown). The proximal shaft connector secures an electrosurgical cable to forceps 10 such that the user may selectively apply electrosurgical energy to the jaw members 110 and 120, respectively. Alternatively, forceps 10 may be configured as a battery-powered instrument.

An activation switch (not shown) may be included that allows a user to selectively apply electrosurgical energy to jaw members 110 and 120 to treat tissue disposed therebetween. More specifically, upon approximation of shaft members 12a, 12b, e.g., when jaw members 110, 120 are moved to the closed position, the activation switch may be activated to supply electrosurgical energy to jaw members 110, 120 such that, upon depression of the activation switch, electrosurgical energy is supplied to sealing surface 112 and/or sealing surface 122 of jaw members 110, 120, respectively, to seal tissue grasped therebetween. Standardized activation switches are contemplated, e.g., in-line switches, finger switches, toggle switches, foot switches, etc.

Figure 2:
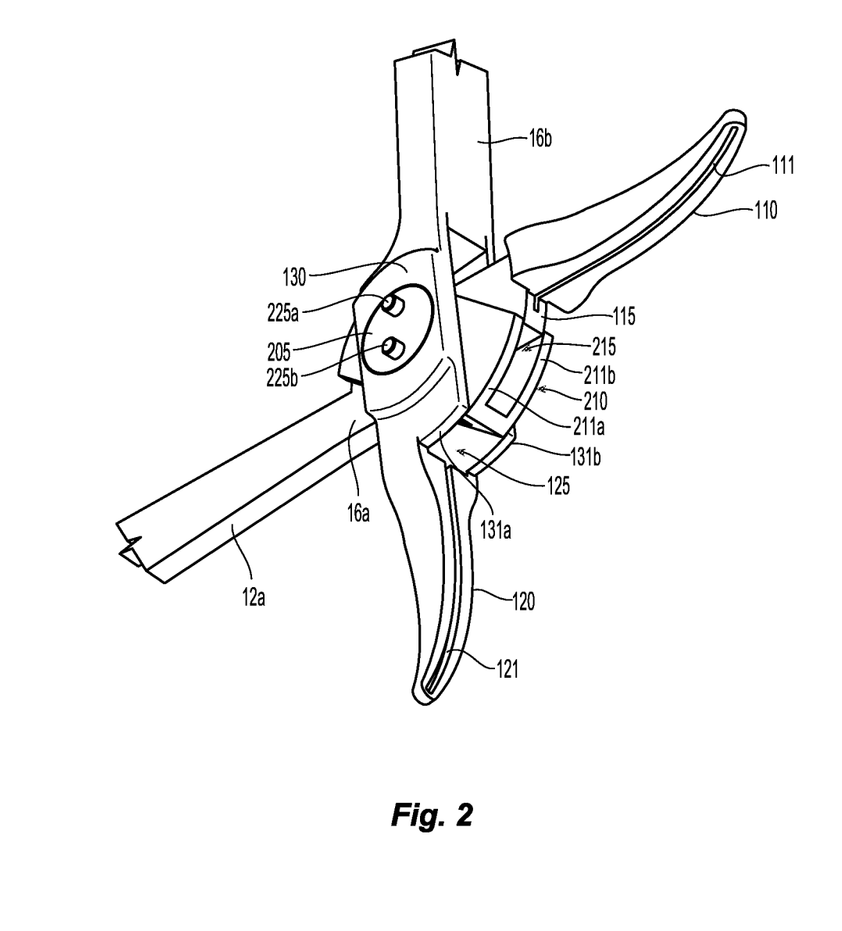
FIG. 2 is an enlarged, perspective view of the distal end of the forceps of FIG. 1.
Figure 3:
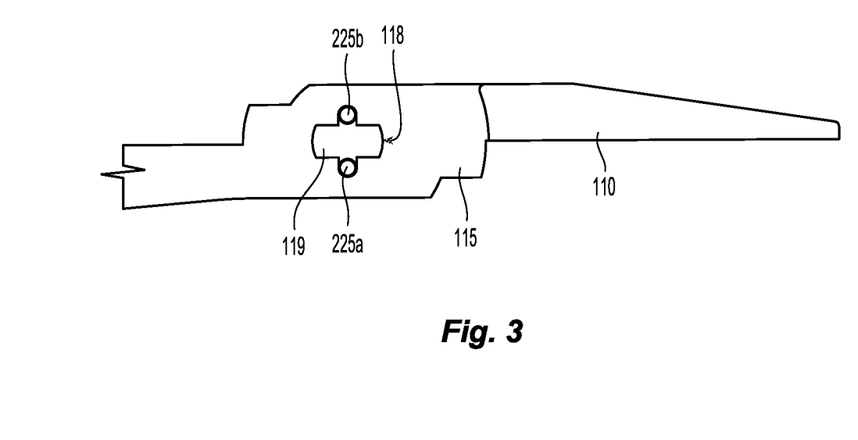
FIG. 3 is an enlarged, side view of a portion of a first jaw member of an end effector assembly of the forceps of FIG. 1.

Referring to FIGS. 1-5, shaft 12a and 12b are configured to rotate about pivot assembly 200 from the first, spaced position to the second, closer position for grasping tissue. Pivot assembly 200 include a pair of pivot pins 225a and 225b that is configured to extend from a proximal flange 115 on either side of jaw member 110 (see FIG. 2). More specifically and as best shown in FIG. 3, pivot pins 225a and 225b are part of a pivot post 119 that is configured to engage within an aperture 118 defined within the proximal flange 115 of jaw member 110. Pivot post 119 may engage aperture 118 in any known manner, e.g., snap-fit, injection molded, overmolded, etc. or be integrally defined therewith, e.g., machined. The pivot post 119 extends from either side of flange 115 such that pivot pins 225a and 225b extend from either side of the flange 115 the purpose of which being explained in more detail below.

Figure 4:
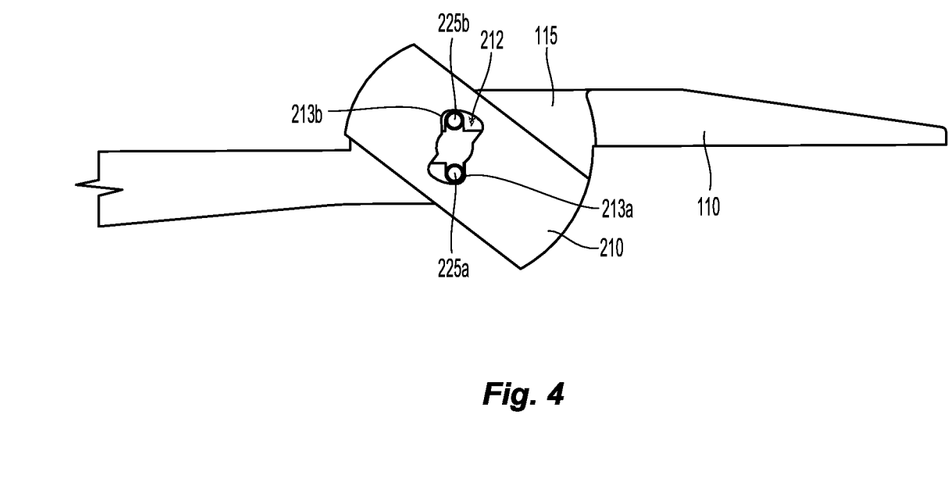
FIG. 4 is an enlarged, side view of a guard member of the end effector assembly of the forceps of FIG. 1 coupled with the first jaw member.

FIGS. 2 and 4 show the positioning of a guard 210 atop the pivot pins 225a and 225b. Guard 210 defines a generally U-shaped transverse cross-sectional configuration including legs 211a and 211b that are configured to surround proximal flange 115 and engage pivot post 119 extending from either side thereof. Guard 210 includes a generally hourglass-shaped aperture 212 defined within each leg 211a, 211b thereof that are configured to engage pivot pins 225a and 225b at respective ends thereof. The hourglass-shaped configuration of aperture 212 allows the guard 212 to rotate about pivot pins 225a and 225b in an angular fashion when jaw members 110 and 120 are moved from the spaced apart position to the closer position to engage tissue. The hourglass configuration also forms one or more stops 213a and 213b that limit the angular rotation of the guard 210 when moving from the closer position to the open position. Guard 210 is also configured to eliminate any gap between proximal flanges 115, 130 of jaw members 110, 120, respectively, that may form during rotation of the two jaw members 110 and 120 relative to one another which can create undesirable pinch points therebetween for catching tissue.

Figure 5:
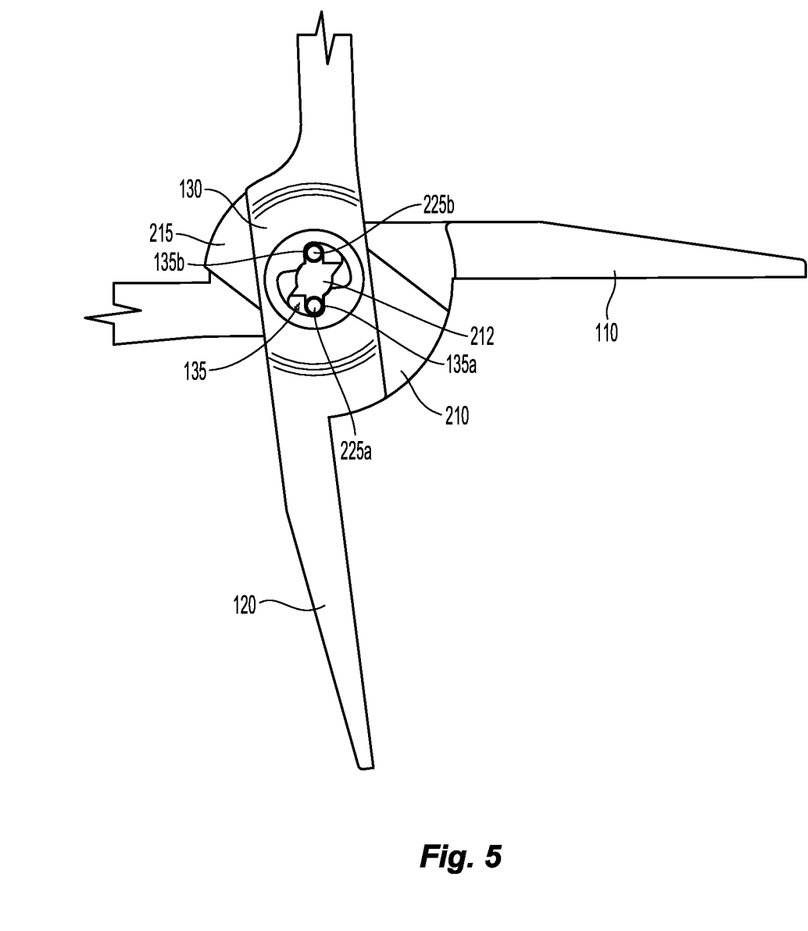
FIG. 5 is an enlarged, side view of the guide member, the first jaw member, and a portion of a second jaw member of the end effector assembly of the forceps of FIG. 1 coupled with one another.

FIG. 5 shows the relative positioning of jaw member 120 surrounding guard 210. More particularly, the proximal flange 130 of jaw member 120 includes a generally U-shaped transverse cross-sectional configuration having legs 131a and 131b that define a slot 125 therein that is configured to receive both legs 211a and 211b of U-shaped guard 210 (See FIG. 2). Each leg 131a and 131b of proximal flange 130 includes a generally hourglass-shaped aperture 135 defined therein that is configured to engage pivot pins 225a and 225b at respective ends thereof. The hourglass configuration also forms one or more stops 135a and 135b that limit the angular rotation of the jaw member 120 when moving from the closer position to the open position. Aperture 135 is a similar hourglass-shape to aperture 212 but is larger to allow jaw member 120 to angularly rotate further than guard 210 to enable the jaw members 110 and 120 to open wider while also avoiding pinch points due to guard 210. In other words and as best seen in FIG. 5, the angular rotation of the pivot pins 225a and 225b within aperture 135 of jaw member 120 extends beyond the angular rotation of the pivot pins 225a and 225b within the guard 210 such that, when opening the jaw members 110 and 120, the pivot pins 225a and 225b bottom out within aperture 212 of guard 210 well before the pivot pins 225a and 225b bottom out within aperture 135. Other configurations of the apertures 135 and 212 are contemplated that are designed to constrain the jaw members 110 and 120 to a specific angle relative to the pivot assembly to accomplish the purpose of increasing the degree of rotation of the jaw members 110 and 120.

FIG. 5 shows the assembled configuration of the pivot assembly 200 with the jaw members 110 and 120 disposed in the spaced apart position. Guard 210 receives flange 115 in slot 215 and seats within slot 125 of proximal flange 130. A pivot plate 205 is engaged with the pivot pins 225a and 225b and acts to prevent the ingress of surgical fluids into the pivot assembly 200. As second pivot plate (not shown) is disposed on the opposite of the pivot assembly 200 for similar purposes.

Forceps 10 may further include a knife assembly (not shown) disposed within one of the shaft members, e.g., shaft member 12a, and a knife channel 111, 121 (FIG. 2) defined within one or both of jaw members 110, 120, respectively, to permit reciprocation of a knife (not shown) therethrough. A trigger (not shown) may be coupled to one of the shafts, e.g., shaft 12a, for advancing the knife from a retracted position within shaft member 12a to an extended position wherein the knife extends into knife channels 111, 121 to divide tissue grasped between jaw members 110, 120. The pivot pins 225a and 225b are configured to allow reciprocation of the knife therebetween. As best shown in FIG. 5, the knife of the knife assembly would only be advanceable when the jaw members 110 and 120 are disposed in the closer position since it would be necessary for the U-shaped guard 210 and U-shaped proximal flange 130 to align for reciprocation of the knife. Thus, U-shaped guard 210 provides additional functionality as a knife safety lockout.

In the fully assembled condition as shown in FIGS. 2 and 5, jaw members 110, 120 are disposed in opposed relation relative to one another such that, upon movement of jaw members 110, 120 to the closer position, tissue is grasped therebetween. Accordingly, in use, electrosurgical energy may be supplied to one or both of electrically-conductive sealing surfaces 112 and 122 of jaw members 110 and 120, respectively, and conducted through tissue to seal tissue grasped therebetween. The knife may thereafter or otherwise be advanced through knife channels 111, 121 of jaw members 110, 120 to cut tissue grasped therebetween. The orientation of the guard 210, as detailed above, avoids creating pinch points during angular rotation of the jaw members 110 and 120 between the open and closer positions.

From the foregoing and with reference to the various figure drawings, those skilled in the art will appreciate that certain modifications can also be made to the present disclosure without departing from the scope of the same. For example, the generally U-shaped guard 210 of the present disclosure may be replaced with a different geometric configuration that rotates as the various jaw member components move to increase the overall range of the jaw members 110 and 120 when opened. Half U-shaped configurations, nestled configurations, offset configurations, multicomponent configurations, etc. are all contemplated. Moreover, the jaw members 110 and 120 and/or a combination of the jaw members 110 and 120 and guard 210 may include various geometric configurations to accomplish the same purpose, i.e., increasing the overall opening range of the jaw members 110 and 120. Although two discreet pivot pins 225a, 225b are described herein, a single pin with an eccentric cross section (not shown) may be configured to achieve the same effect. Moreover, the pivot assembly 200 may be more simply configured to include one (or multiple) protrusions that are dimensioned to engage the proximal flanges of the jaw members 110 and 120 and guard 210 to define a rotational axis.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. An end effector assembly for a forceps, comprising:
    first and second jaw members, each of the jaw members including a proximal flange extending therefrom, each proximal flange defining an aperture extending therethrough receiving a pivot assembly including first and second pivot pins, the proximal flange of the second jaw member including a U-shaped cross section having first and second legs defining a slot therebetween; and
    a guard disposed between the proximal flanges of the first and second jaw members, the guard having a U-shaped cross section with first and second legs receiving the proximal flange of the first jaw member and seat within the slot of the proximal flange of the second jaw member, the guard eliminating gaps between the proximal flanges of the first and second jaw members during angular rotation of the first and second jaw members between a first, spaced apart position and a second, closer position.

2. The end effector assembly of claim 1 wherein the guard includes an aperture defined therein receiving the first and second pivot pins, the guard rotatable about the first and second pivot pins during movement of the jaw members between the first and second positions.

3. The end effector assembly of claim 2 wherein the aperture of the guard is hourglass-shaped defining a stop that is limiting angular rotation of the guard when the jaw members are moved from the second position to the first position.

4. The end effector assembly of claim 1 wherein an aperture defined in the proximal flange of the second jaw member is hourglass-shaped defining a stop that is limiting angular rotation of the second jaw member when the jaw members are moved from the second position to the first position.

5. The end effector assembly of claim 3 wherein an aperture defined in the proximal flange of the second jaw member is hourglass-shaped defining a stop that is limiting angular rotation of the second jaw member when the jaw members are moved from the second position to the first position.

6. The end effector assembly of claim 5 wherein the hourglass-shaped aperture in the proximal flange of the second jaw member is larger than the hourglass-shaped aperture in the guard such that the degree of angular rotation of the second jaw member is greater than the degree of angular rotation of the guard.

7. The end effector assembly of claim 1 wherein the pivot assembly is mechanically engaged to the proximal flange of the first jaw member by snap-fit, overmolding, injection molding or friction fit.

8. The end effector assembly of claim 1 wherein the pivot assembly is integrally associated with the proximal flange of the first jaw member.

9. The end effector assembly of claim 1 wherein the first and second pivot pins extend on either side of the pivot assembly to pivotably engage both legs of the guard and both legs of the proximal flange of the second jaw member.

10. The end effector assembly of claim 3 wherein at least one of the first or second pivot pins abuts the stop on the aperture of the guard to limit angular rotation of the guard when the first and second jaw members move from the second to first positions.

11. The end effector assembly of claim 4 wherein at least one of the first or second pivot pins abuts the stop on the aperture of the proximal flange of the second jaw member to limit angular rotation of the first and second jaw members from the second to first positions.

12. A forceps, comprising:
first and second shaft members;
the first shaft member including a first jaw member at a distal end thereof and the second shaft member including a second jaw member at a distal end thereof, the first and second jaw members disposed in opposing relation relative to one another and movable about a pivot assembly from a first, spaced apart position to a second, closer position for grasping tissue, each of the jaw members including a proximal flange extending therefrom, each proximal flange defining an aperture extending therethrough receiving the pivot assembly, the proximal flange of the second jaw member having a U-shaped cross section having first and second legs defining a slot therebetween; and
a guard disposed between the proximal flanges of the first and second jaw members, the guard having a U-shaped cross section with first and second legs receiving the proximal flange of the first jaw member and seat within the slot of the second jaw member, the guard eliminating gaps between the proximal flanges of the first and second jaw members during angular rotation of the first and second jaw members between the first and second positions.

13. The forceps of claim 12 wherein the guard includes an aperture defined therein receiving first and second pivot pins of the pivot assembly, the guard rotatable about the first and second pivot pins during movement of the jaw members between the first and second positions.

14. The forceps of claim 13 wherein the aperture of the guard is hourglass-shaped defining a stop that is limiting angular rotation of the guard when the jaw members are moved from the second position to the first position.

15. The forceps of claim 12 wherein an aperture defined in the proximal flange of the second jaw member is hourglass-shaped defining a stop that is limiting angular rotation of the second jaw member when the jaw members are moved from the second position to the first position.

16. The forceps of claim 14 wherein an aperture defined in the proximal flange of the second jaw member is hourglass-shaped defining a stop that is limiting angular rotation of the second jaw member when the jaw members are moved from the second position to the first position.

17. The forceps of claim 16 wherein the hourglass-shaped aperture in the proximal flange of the second jaw member is larger than the hourglass-shaped aperture in the guard such that the degree of angular rotation of the second jaw member is greater than the degree of angular rotation of the guard.

18. The forceps of claim 12 wherein the pivot assembly is mechanically engaged to the proximal flange of the first jaw member by snap-fit, overmolding, injection molding or friction fit.

19. The forceps of claim 12 wherein the pivot assembly includes first and second pivot pins that extend on either side thereof to pivotably engage both legs of the guard and both legs of the proximal flange of the second jaw member.

* * * * *